(12) United States Patent
Mattchen

(10) Patent No.: US 11,839,366 B2
(45) Date of Patent: Dec. 12, 2023

(54) HIGH TENSION SUTURE ANCHOR

(71) Applicant: Kinamed, Inc., Camarillo, CA (US)

(72) Inventor: Terry Mattchen, Scottsdale, AZ (US)

(73) Assignee: Kinamed, Inc., Camarillo, CA (US)

( * ) Notice: Subject to any disclaimer, the term of this patent is extended or adjusted under 35 U.S.C. 154(b) by 1069 days.

(21) Appl. No.: 16/429,456

(22) Filed: Jun. 3, 2019

(65) Prior Publication Data

US 2019/0290257 A1    Sep. 26, 2019

Related U.S. Application Data

(63) Continuation of application No. 15/234,823, filed on Aug. 11, 2016, now Pat. No. 10,307,152, which is a continuation-in-part of application No. 13/783,061, filed on Mar. 1, 2013, now abandoned.

(60) Provisional application No. 61/741,792, filed on May 14, 2012.

(51) Int. Cl.
| | | |
|---|---|---|
| *A61B 17/04* | (2006.01) | |
| *A61B 17/88* | (2006.01) | |
| *A61B 17/82* | (2006.01) | |
| *A61B 17/84* | (2006.01) | |

(52) U.S. Cl.
CPC .......... *A61B 17/0401* (2013.01); *A61B 17/82* (2013.01); *A61B 17/842* (2013.01); *A61B 17/8869* (2013.01); *A61B 2017/0403* (2013.01); *A61B 2017/0409* (2013.01)

(58) Field of Classification Search
CPC . A61B 17/0401; A61B 17/82; A61B 17/8869; A61B 17/68; A61B 2017/0456; A61B 2017/045; A61B 2017/0403; A61B 2017/0409; F16G 11/048; F16G 11/05; F16G 11/101

See application file for complete search history.

(56) References Cited

U.S. PATENT DOCUMENTS

| | | | |
|---|---|---|---|
| 1,945,438 A | | 1/1934 | Landahl |
| 2,934,364 A | | 4/1960 | Conversy |
| 3,254,383 A | * | 6/1966 | Ehmann .................. F16G 11/05 403/275 |
| 3,600,765 A | | 8/1971 | Rovinsky et al. |
| 3,952,377 A | | 4/1976 | Morell |
| 4,368,999 A | | 1/1983 | Morel |
| 4,455,717 A | | 6/1984 | Gray |
| 4,507,008 A | | 3/1985 | Adl et al. |
| 6,086,608 A | * | 7/2000 | Ek ...................... A61B 17/0487 606/301 |

(Continued)

FOREIGN PATENT DOCUMENTS

| | | | |
|---|---|---|---|
| EP | 0591991 | 4/1994 | |
| WO | WO-9730639 A1 * | 8/1997 | ......... A61B 17/0487 |
| WO | WO 2010/014119 | 2/2010 | |

*Primary Examiner* — Anh T Dang

(74) *Attorney, Agent, or Firm* — Warner Norcross + Judd LLP

(57) ABSTRACT

The present invention describes a bio-medically compatible gripping device capable of radial collapse in accordance with the shrinkage of a nylon or other polymeric material cored surgical cable undergoing tension while maintaining a firm grip for prolonged periods of time. It provides a gripping device capable of maintaining a non-damaging hold on the outer surface of a slippery delicate cable under high tension for a sufficient time in which the healing process can occur.

23 Claims, 13 Drawing Sheets

(56) References Cited

U.S. PATENT DOCUMENTS

2008/0177291 A1     7/2008   Jensen et al.
2011/0112550 A1     5/2011   Heaven et al.

* cited by examiner

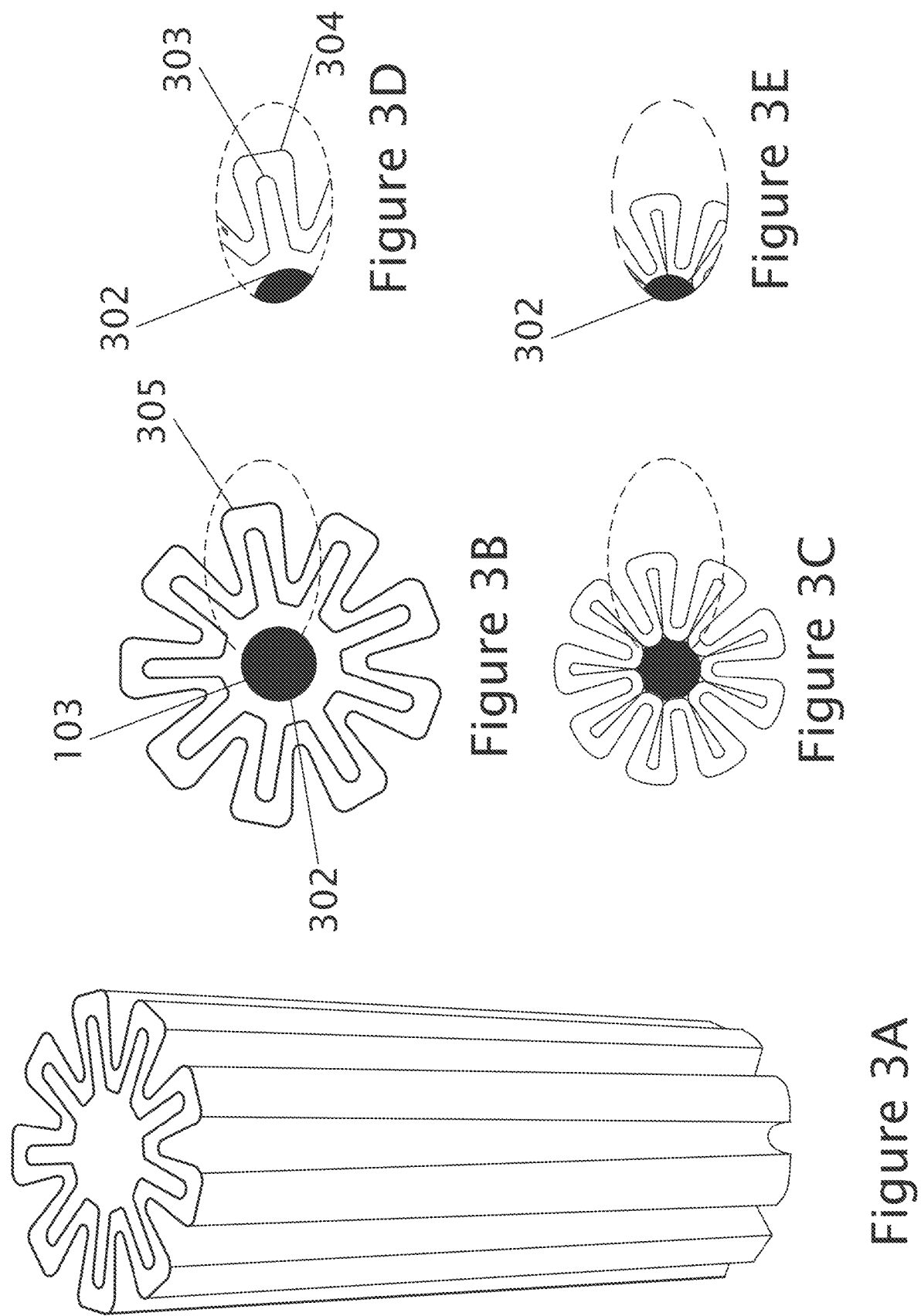

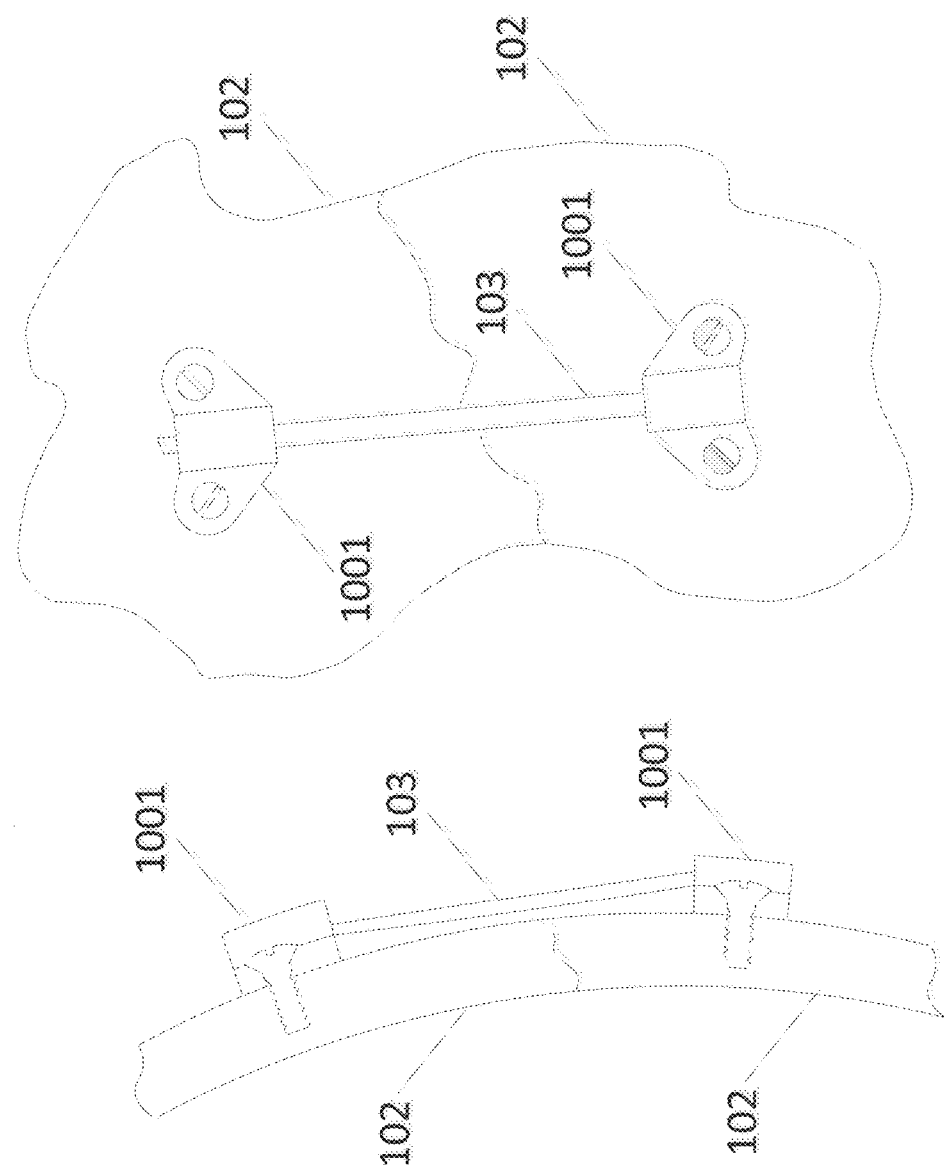

HIGH TENSION SUTURE ANCHOR

CROSS-REFERENCE TO RELATED APPLICATIONS

This application is a continuation of U.S. patent application Ser. No. 15/234,823, filed Aug. 11, 2016, which is a Continuation-In-Part of U.S. patent application Ser. No. 13/783,061, filed Mar. 1, 2013, which claims priority to Provisional Patent Application No. 61/741,792, filed May 14, 2012, the contents of each are herein incorporated by reference in their entireties.

BACKGROUND

Field of the Invention

This invention relates to devices for retaining surgical cables under high tension.

Description of the Related Art

Present day polymer based surgical cables seem to defy all attempts to engage and lock under high tension, thereby dramatically curtailing their range of practical use. Cable locks such as described in U.S. Pat. No. 7,625,373 attempt to solve the just such a problem. U.S. Pat. No. 7,625,373 is a typical example of the use of a wedge as a simple machine for securement.

Material properties of polymer fibers tend to complicate the situation. Surfaces tend to be slippery and materials have hysteresis. In some circumstances the materials tend to deform and flow (as implied by the common term "plastic"). Conventional knots are inadequate, clasps and fasteners slip under high tension. Attempts to counteract slippage by application of increased pressure often result in cutting or fraying of the cable. Despite their usefulness, widespread acceptance of polymer cables depends in part on the availability of an efficient, economical, convenient, and reliable means of clamping and retaining under moderate to high tension.

Nevertheless, as disclosed in U.S. Pat. No. 6,589,246 (herein incorporated by reference), certain polymer cables have shown promise for surgical use. The cable (10) of the '246 patent, shown in FIG. 6, is a composite. The nylon or other polymeric material core (14) comprises about 75% of the diameter of the finished cable; the high strength UHMW polyethylene fibers (15) braided onto the core comprise the remaining 25%. The difficulties that are unique to gripping such braided polymer cable over the conventional steel cable are the following:

The polymer cable stretches under high tension. As tension is applied, the diameter of the nylon or other polymeric material core shrinks by approximately 12% Thus, the gripping device must be flexible enough to collapse correspondingly, all the while maintaining a still firmer grip on the cable. By contrast, prior art steel cables do not shrink under tension, thereby obviating the need for a flexibly collapsing gripping mechanism.

The fibers of the braided jacket do not stretch along with the core. Because such fibers are extremely delicate. (i.e., each fiber having a diameter measuring only a few ten-thousandth's of an inch), they will break if not gripped gently and uniformly about their circumference. By contrast, prior art steel cables have a robust metallic surface and are therefore not sensitive to asymmetric gripping.

Finally, the polyethylene fibers of the jacket are quite slippery, and so must be held gently, uniformly, and yet still quite firmly.

In essence, the force F required to retain such a cable must be applied in such a way that the cable does not cause damage, yet be of sufficiently significant magnitude to maintain a grip under high tension as the healing process evolves.

One way to accomplish this goal is to apply the force over a large surface area. For example, a force of 30 lbs. can be offset by a cumulative pressure of 3000 psi over a cumulative area of 0.01 square inches, or, a cumulative pressure of 300 psi over an area of 0.10 square inches. The latter is a more optimal choice given the delicate nature of the cables involved as it distributes the pressure over a larger area, thereby minimizing possible damage. In the real world, this goal is extremely difficult to achieve due the high forces involved, the extremely small dimensions required, and the delicacy of the cable itself. In more specific terms, the cumulative force, $F_{total}$, can be expressed as:

$$F_{total} = \int \left(\frac{dP}{da}\right) da$$

Where $$\frac{dP}{da}$$

is the applied pressure at the surface increment da, the integral being taken over the entire contacting surface area. The present invention exploits the topology of the two parameters, $$\frac{dP}{da}$$

and da so as to maximize the total retaining force on the cable while minimizing the necessary pressure at each point.

SUMMARY

The above concerns are met by a surgical cartridge comprised of two components, a cartridge and an insert able collet with a star-shaped cross section. The collet is hollow and conically shaped on both the inside and outside surfaces, has an insertion end, and an exposed end. While the diameter of the outside surface is larger at the exposed end than at the insertion end, the diameter of the inside surface is smaller at the exposed end than at the insertion end.

The collet of the present design is comprised of several gripping fingers that move radially inward to grip the cable. The fingers close in on the cable in a uniform manner, while maintaining as much contact area as possible. This design is further optimized by the number of fingers, the thickness of the resulting finger wall vs. the size of the cable and surgical cartridge. In essence, a delicate balance must be achieved between the number of fingers and the thickness of the finger wall.

In an alternate embodiment the collet has a set of outside fingers, inside fingers, and intermediate fingers. There are an equal number of inside and intermediate fingers, and twice as many outside fingers. Each of the outside fingers are flanked by an inside finger and an intermediate finger. The shorter intermediate fingers allow space so that the inside fingers can be shaped to maximize contact with the outside surface of the surgical cable.

It is an objective of the present invention to provide a gripping device capable of providing a firm, gentle, and uniform pressure to a surgical cable comprised of a nylon or other polymeric material core covered by a polyethylene fiber braid.

It is a further objective of this invention to provide a gripping device that is biomedically compatible with the human body.

It is a still further objective of this invention to provide a gripping device capable of radial collapse in accordance with the shrinkage of a nylon or other polymeric material cored surgical cable undergoing tension while maintaining a firm grip throughout the process.

It is a still further objective of this invention to provide a gripping device capable of maintaining a grip, yet not damage, a delicate cable under high tension for a period of time adequate for the healing process to occur.

A bio-compatible high tension suture anchor capable of providing a consistently uniform pressure of 2500-3500 psi over an area measuring less than 0.05 square inches is disclosed. The bio-compatible high tension suture anchor may further comprise a truncated, hollow, conical cylinder having a length, a radius, and a cylindrical wall. The cylindrical wall may be comprised of a regular series of ridges and valleys parallel to the length of the conical cylinder.

The truncated cylinder further may comprise an insertion end, and an exposed end opposite the insertion end, an outer conical surface and an inner conical surface. The outer conical surface has a first outer diameter at the insertion end and a second outer diameter at the exposed end, with the first outer diameter being smaller than the second outer diameter. On the other hand, while the inner conical surface also has a first inner diameter at the insertion end and a second inner diameter at the exposed end, with the first inner diameter being larger than the second inner diameter.

The anchor may also comprise a retaining collar operable for progressively compressing the radius of the conical cylinder upon insertion of the conical cylinder within the retaining collar.

The regular series of ridges and valleys may define a radial arrangement of compressive fingers, the fingers being operable for radially uniform compression of a cable inserted within the hollow space of the conical cylinder. The radially uniform compression may be consistent over cable diameter shrinkages of up to 15%. The radial fingers may have a wall thickness of 0.005-0.015 inches. Additionally, the anchor may have a set of outside fingers, a set of inside fingers, and a set of intermediate fingers, wherein each of said outside fingers is flanked by one inside finger and one intermediate finger.

The high tension suture may be made of a metallic alloy. The metallic alloy may be titanium.

The bio-compatible high tension suture anchor may also have a crimping tube integral with the suture anchor and parallel to the length of the conical cylinder. Alternatively, it may include a pair of opposing attachment tabs integral with the suture anchor and perpendicular to the length of the conical cylinder.

An exemplary installation tool for deployment of the high tension suture anchor is also described and claimed. The tool comprises an upper forked member and a lower forked member. The upper forked member and the lower forked member are configured in a scissor-like fashion. The lower forked member is operable for securing and positioning the high tension suture anchor. The tool also comprises an auxiliary lever operable for gripping a surgical cable threaded through the high tension suture anchor and a positioning conduit operable for positioning and tightening a surgical cable to the desired level of tension. The tool further comprises a tension retaining member operable for maintaining the desired level of tension on the surgical cable throughout the deployment process.

A method of deploying a surgical cable within a fractured bone is described and claimed as well. The method comprises the steps of:
1) Presenting any one of the above described high tension suture anchors,
2) Presenting an installation tool as previously described
3) Positioning the anchor within the tool, thereby forming a tooled anchor assembly,
4) Threading a surgical cable through the tooled anchor assembly,
5) Pressing the anchor assembly through a surgically drilled bone aperture while pulling the surgical cable taut,
6) Squeezing the upper and lower forked members of the installation tool together, while urging the conical cylinder of the anchor into the throat of its retaining collar, thereby gripping and securing the inserted surgical cable,
7) Releasing the tension on the surgical cable.
8) Sliding the upper and lower fork members away from the anchor assembly, and
9) Cutting the extraneous length of the surgical cable.

A method of employing cerclage to an assembly of fractured bones using a surgical cable is also described and claimed. The method comprises the steps of.
1) Presenting a high tension suture anchor having an integrated crimping tube,
2) Presenting an installation tool as previously described,
3) Positioning the anchor within the tool, thereby forming a tooled anchor assembly,
4) Crimping one end of the surgical cable in the crimping tube,
5) Encircling the assembly of fractured bones with the free end of the surgical cable,
6) Threading the free end of the surgical cable through the tooled anchor assembly,
7) Squeezing the upper and lower forked members of the installation tool together, while urging the conical cylinder of the anchor into the throat of its retaining collar, thereby gripping and securing the inserted surgical cable,
8) Releasing the tension on the surgical cable,
9) Sliding the upper and lower fork members away from the anchor assembly, and
10) Cutting the extraneous length of the surgical cable.

A method of deploying a surgical cable to the surface of a fractured bone is described and claimed. The method comprises the steps of:
1) Presenting a high tension suture anchor with opposing tabs,
2) Presenting an installation tool as previously described,
3) Positioning the anchor within the tool, thereby forming a tooled anchor assembly,
4) Threading a surgical cable through the tooled anchor assembly, 5) Pressing the anchor assembly against the surface of the fractured bone such that the opposing tabs lie flat against the bone,
6) Screwing the anchor assembly to the fractured bone using the opposing tabs,
7) Pulling the surgical cable taut,
8) Squeezing the upper and lower forked members of the installation tool together, while urging the conical cylinder of the anchor into the throat of its retaining collar, thereby gripping and securing the inserted surgical cable,
9) Releasing the tension on the surgical cable,
10) Sliding the upper and lower fork members away from the anchor assembly, and
11) Cutting the extraneous length of the surgical cable.

These, other features, and various advantages will be apparent to those skilled in the art from the following detailed description of the preferred embodiments and accompanying drawings.

DETAILED DESCRIPTION OF THE PREFERRED EMBODIMENT

Description of the Figures

10—cable (prior art)
14—polymeric material core (prior art)
15—high strength UHMW polyethylene fiber braid (prior art)
101—surgical cartridge
102—bone fragments
103—surgical cable
104—optional washer
105—outer bone aperture for surgical cable (103)
201—retaining collar
202—collet having a star-shaped cross section
203—central void
302—contacting surface of cable (103)
303—inside surface of collet wall
304—outside surface of collet wall
305—collet finger
401—radial cross section of uncompressed collet with cable (103) inserted
402—radial cross section of collet compressed around cable (103)
501—radial plane near top of collet (202)
502—radial plane approximately one third collet length from the top of collet (202)
503—radial plane approximately two thirds collet length from the top of collet (202)
504—radial plane near bottom of collet (202)
700—exemplary installation tool with cable gripping member (703)
701—upper forked member
702—lower forked member
703—cable gripping member
704—tension retaining member
800—installed suture anchor
801—simple embodiment of installation tool
901—cerclage cartridge
1001—tabbed cartridge

DESCRIPTION OF THE FIGURES

Figure 1:
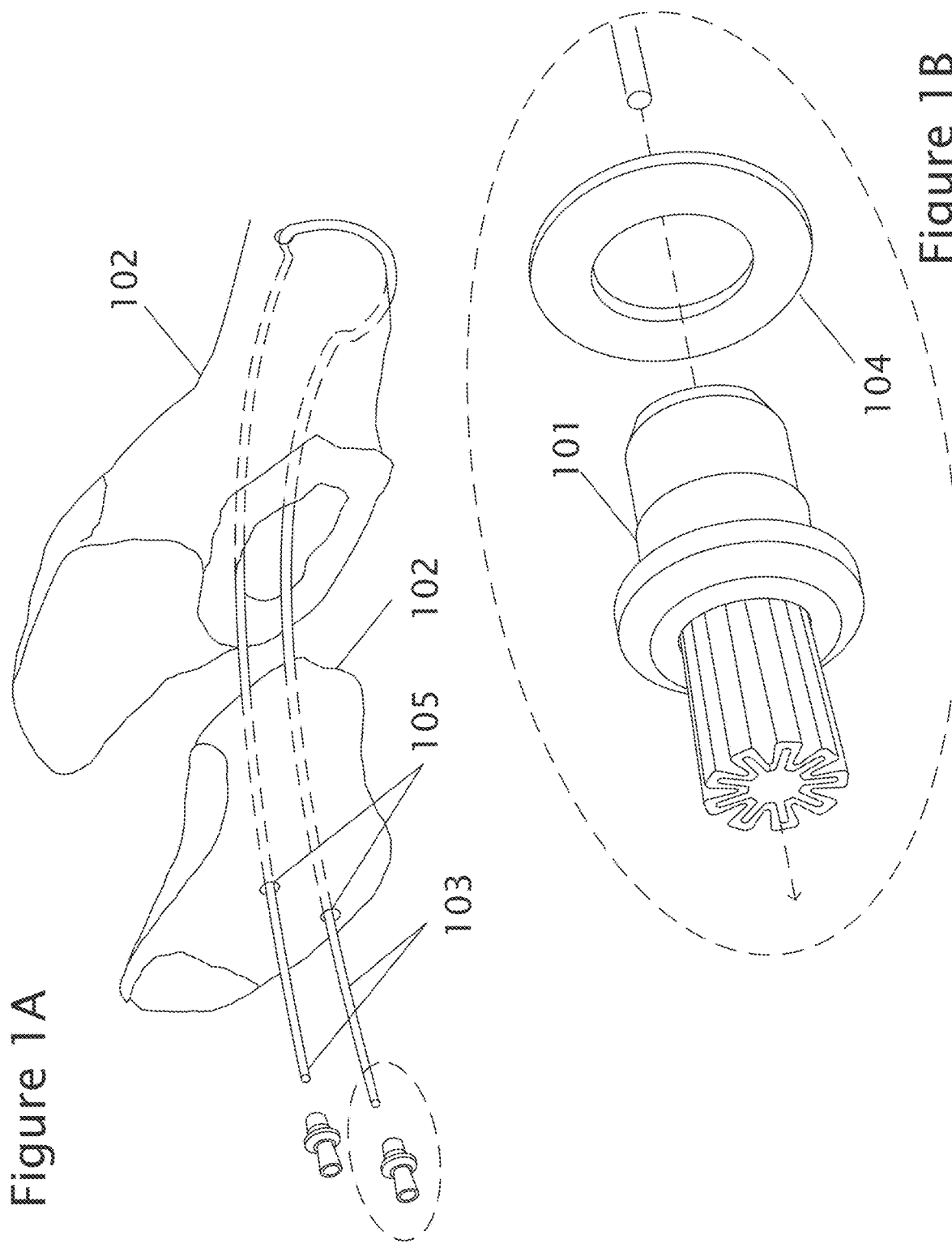

FIGS. 1A and 1B: An illustration of a common scenario, the repair of a fractured olecranon, wherein the surgical cartridge (101) of the present invention is used to secure bone fragments (102). FIG. 1A indicates and overall view. FIG. 1B shows an expanded view of the dotted oval region in FIG. 1A.

Figure 2:
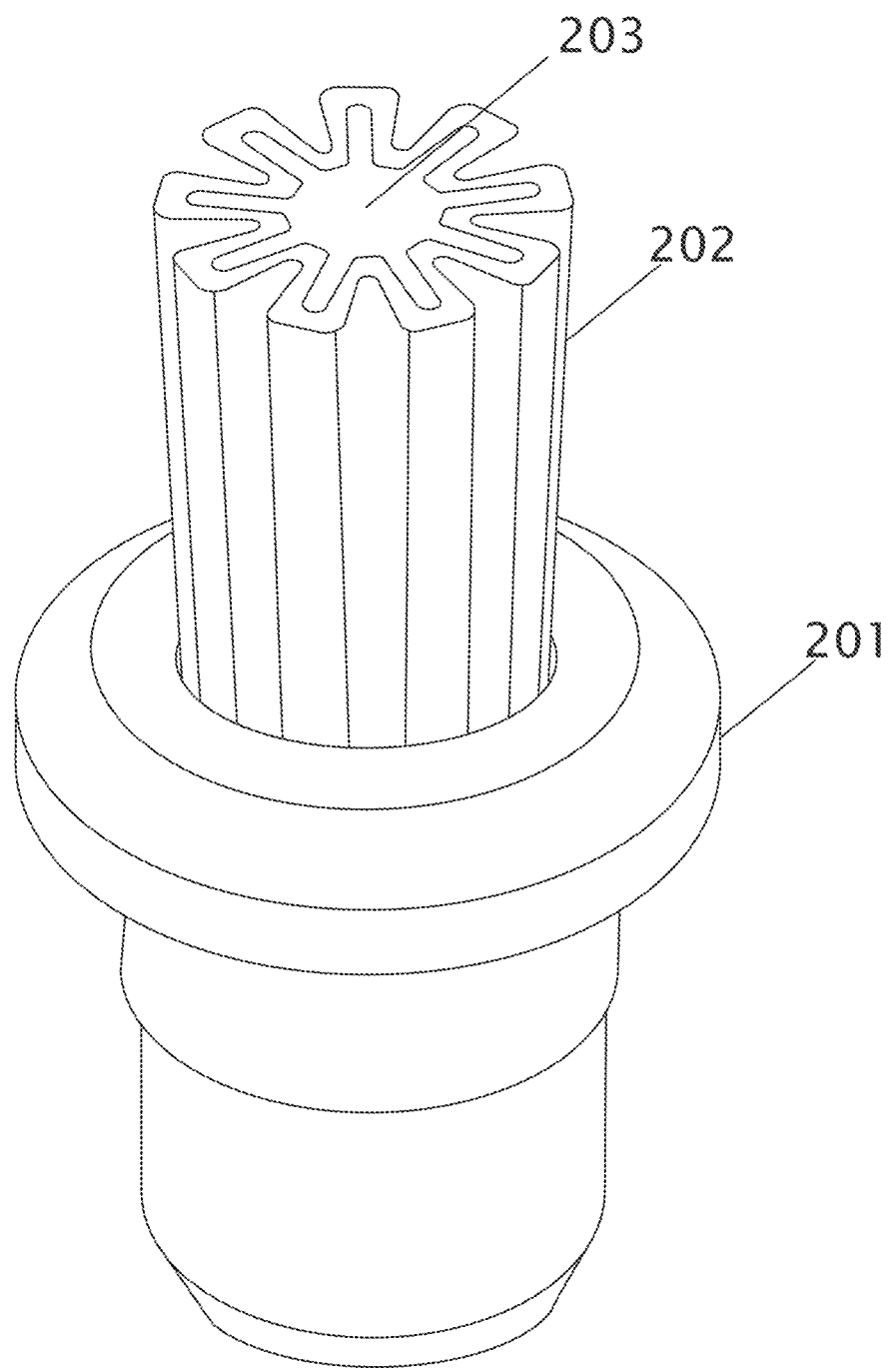

FIG. 2: The surgical cartridge (101) is shown in greater detail. The collet (202) has a star-shaped cross section and surrounds a central void (203) that is enclosed by a retaining collar (201).

FIGS. 3A-3E: The star-shaped collet (202) is shown in greater detail. FIG. 3A indicates a perspective view of the collet (202) and a radial cross section with cable (103) inserted is indicated in FIGS. 3B-3E. The inside (303) and outside (304) surfaces of the wall of each collet finger (305) are indicated as well as the contacting surface (302) of the cable (103).

Figure 4A:
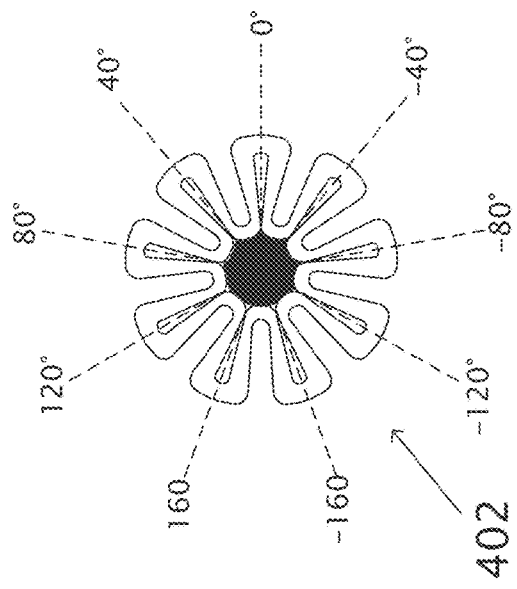
Figure 4B:
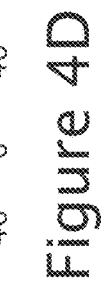
Figure 4C:
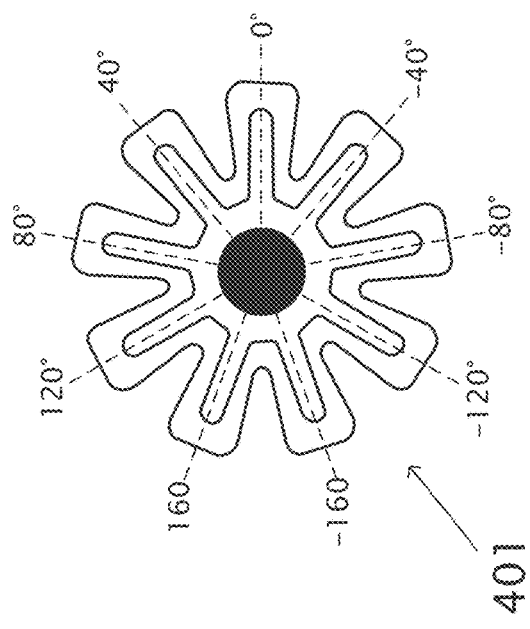
Figure 4D:
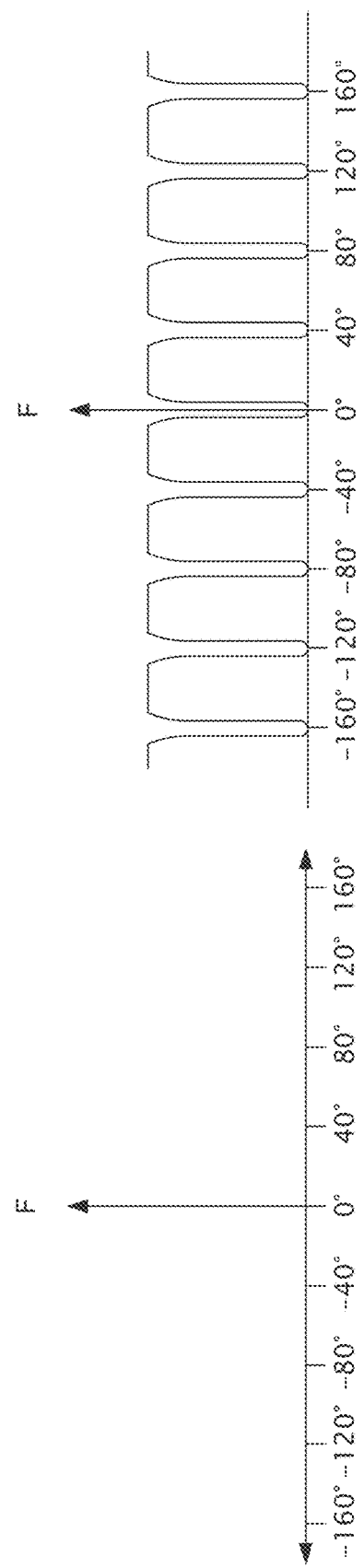

FIGS. 4A-4D: A radial cross section of the star-shaped collet (202) with inserted surgical cable (103) is shown in an uncompressed state (401) in FIG. 4A. Its compressed state (402) is indicated in FIG. 4C. FIGS. 4B and 4D notionally indicate the degree of force area (404) between the collet (202) and surgical cable (103) in FIGS. 4A and 4B, respectively.

Figure 5B:
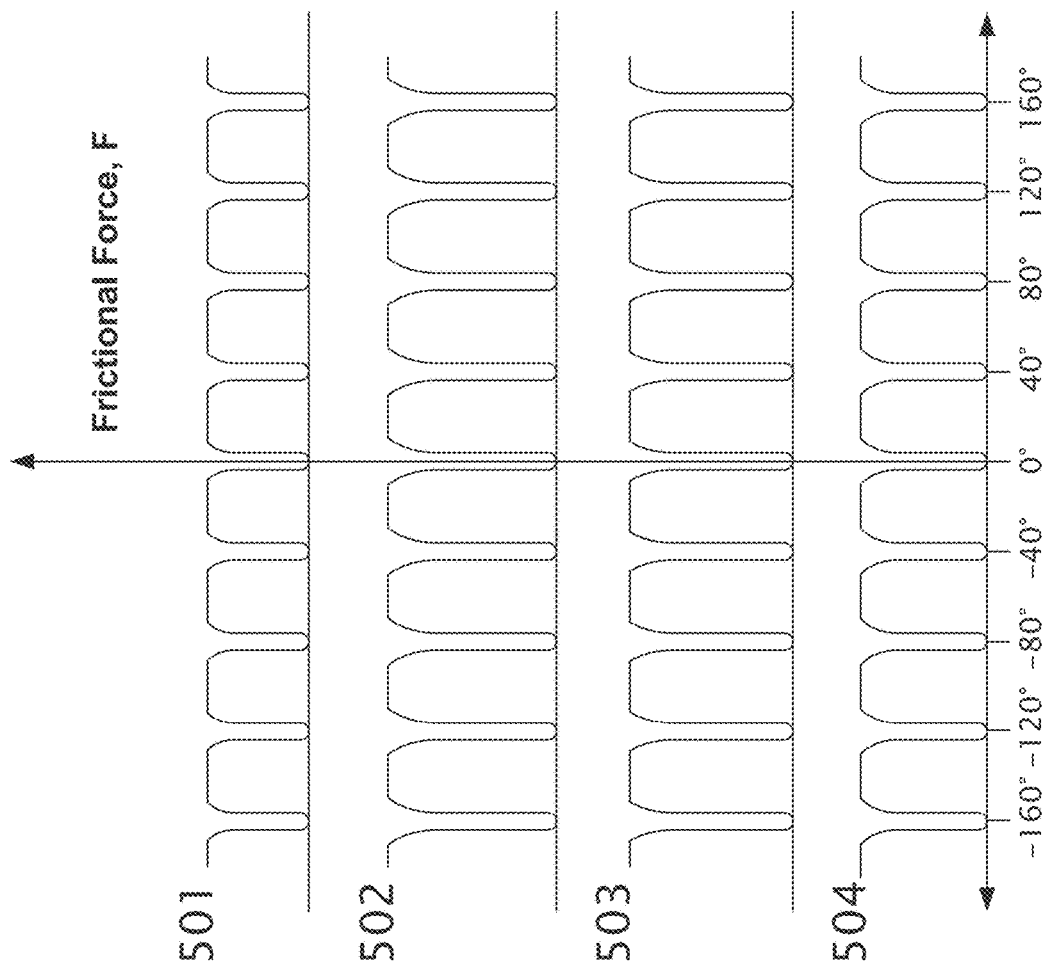
Figure 5A:
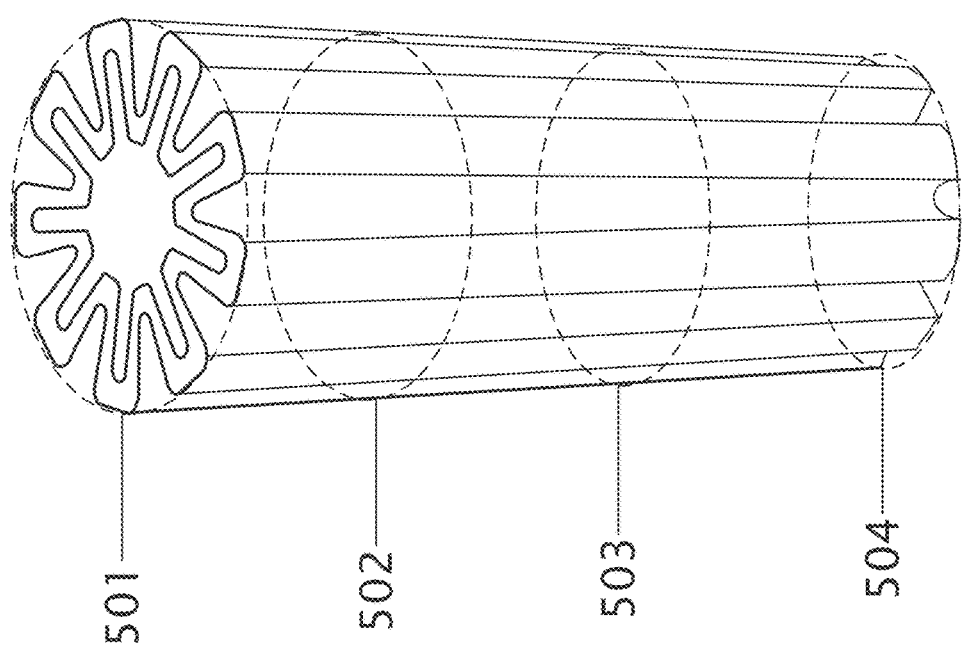

FIGS. 5A and 5B: FIGS. 5A-5B notionally indicate the degree of force area (404) for several positions (501)-(504) along the collet (202) length. The flat tops indicate the saturation of the applied force upon contact with the cable (103) exterior.

Figure 6:
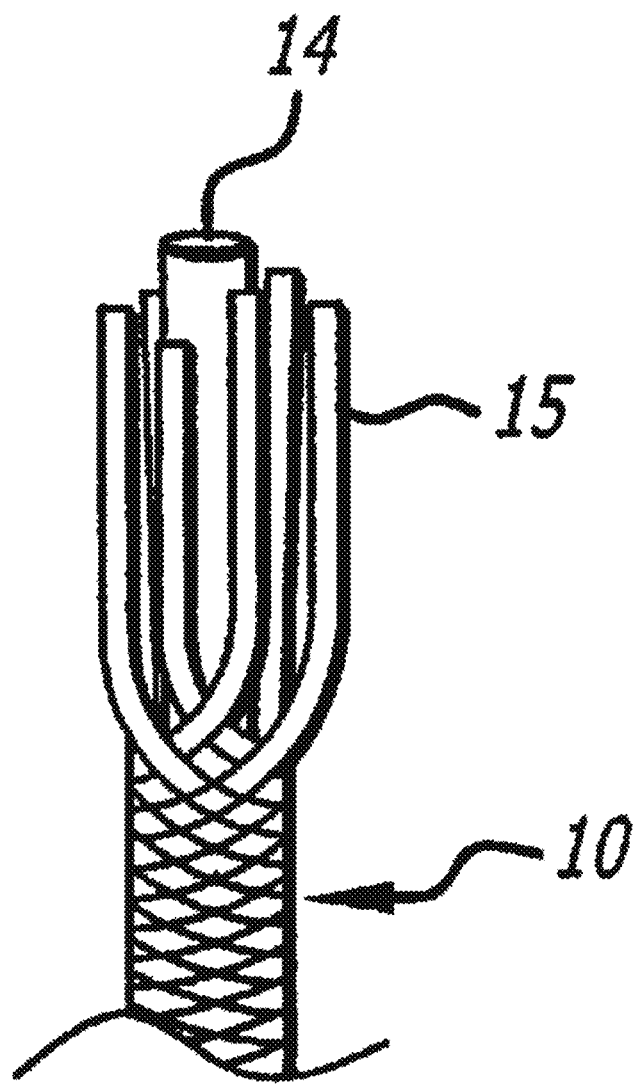

FIG. 6: Prior art cable (10) showing inner core (14) and outer braid (15).

Figure 7:
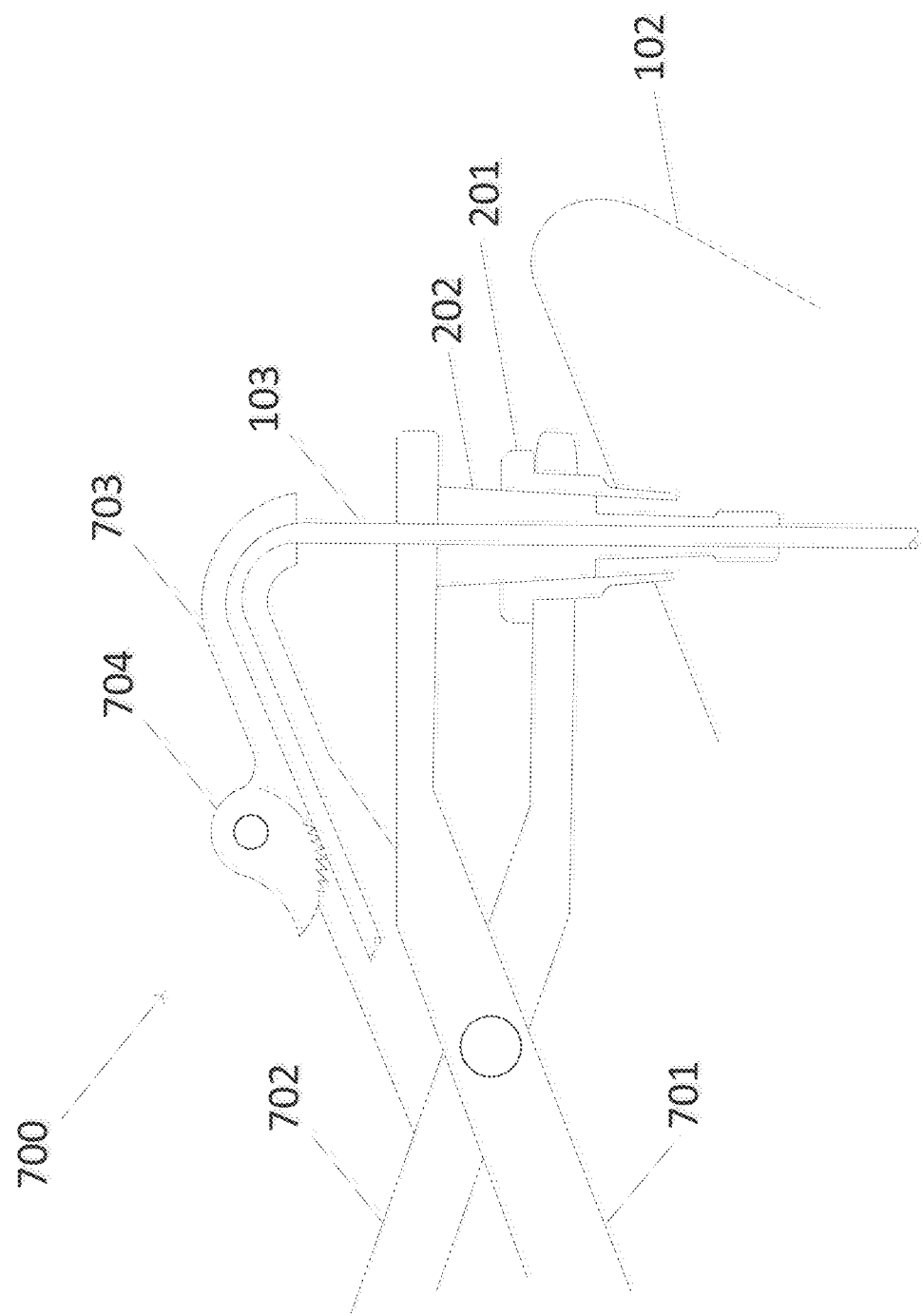

FIG. 7: Tool for installation of surgical cartridge (101) and surgical cable (103) inserted therein.

Figure 8:
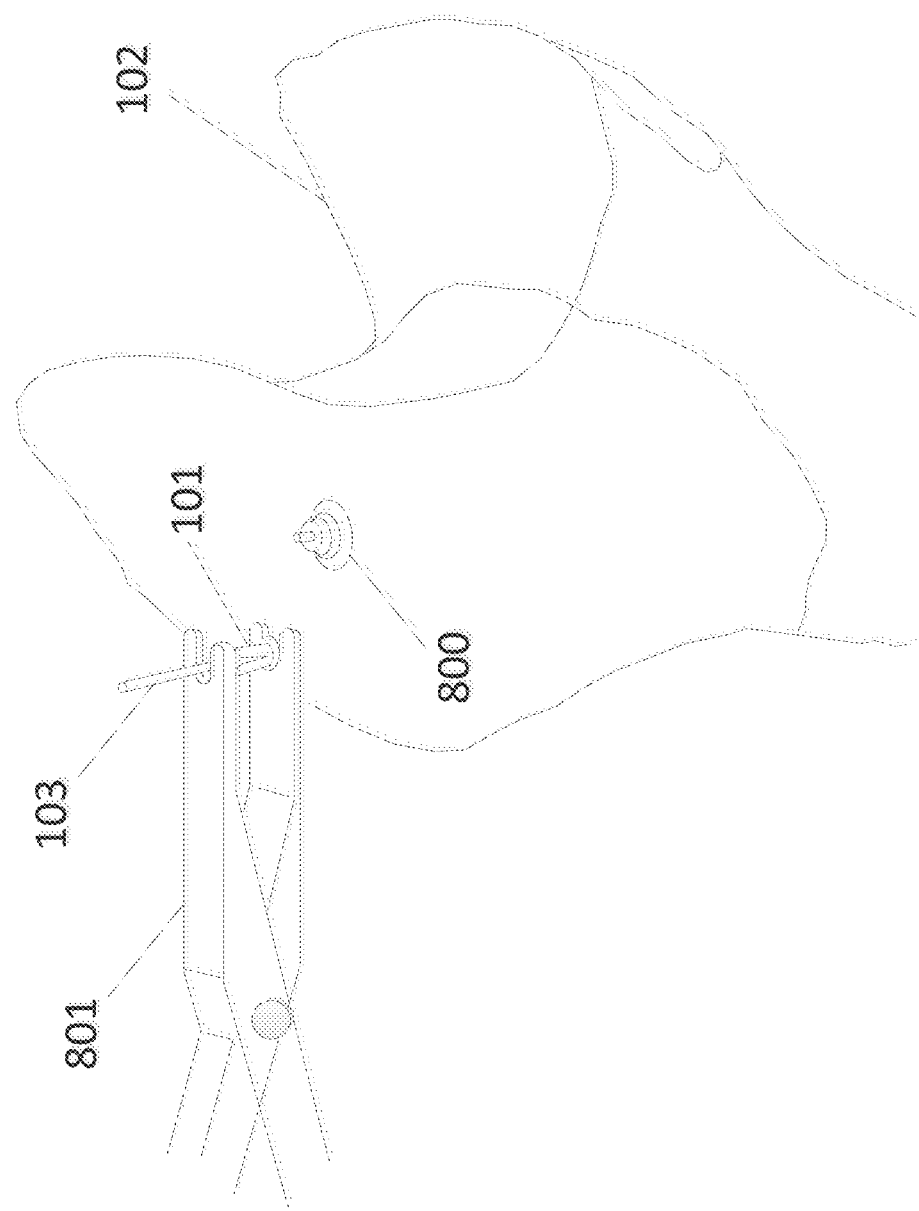

FIG. 8: Installation tool (700) detailing features and use of upper and lower forked members (701), (702).

Figure 9:
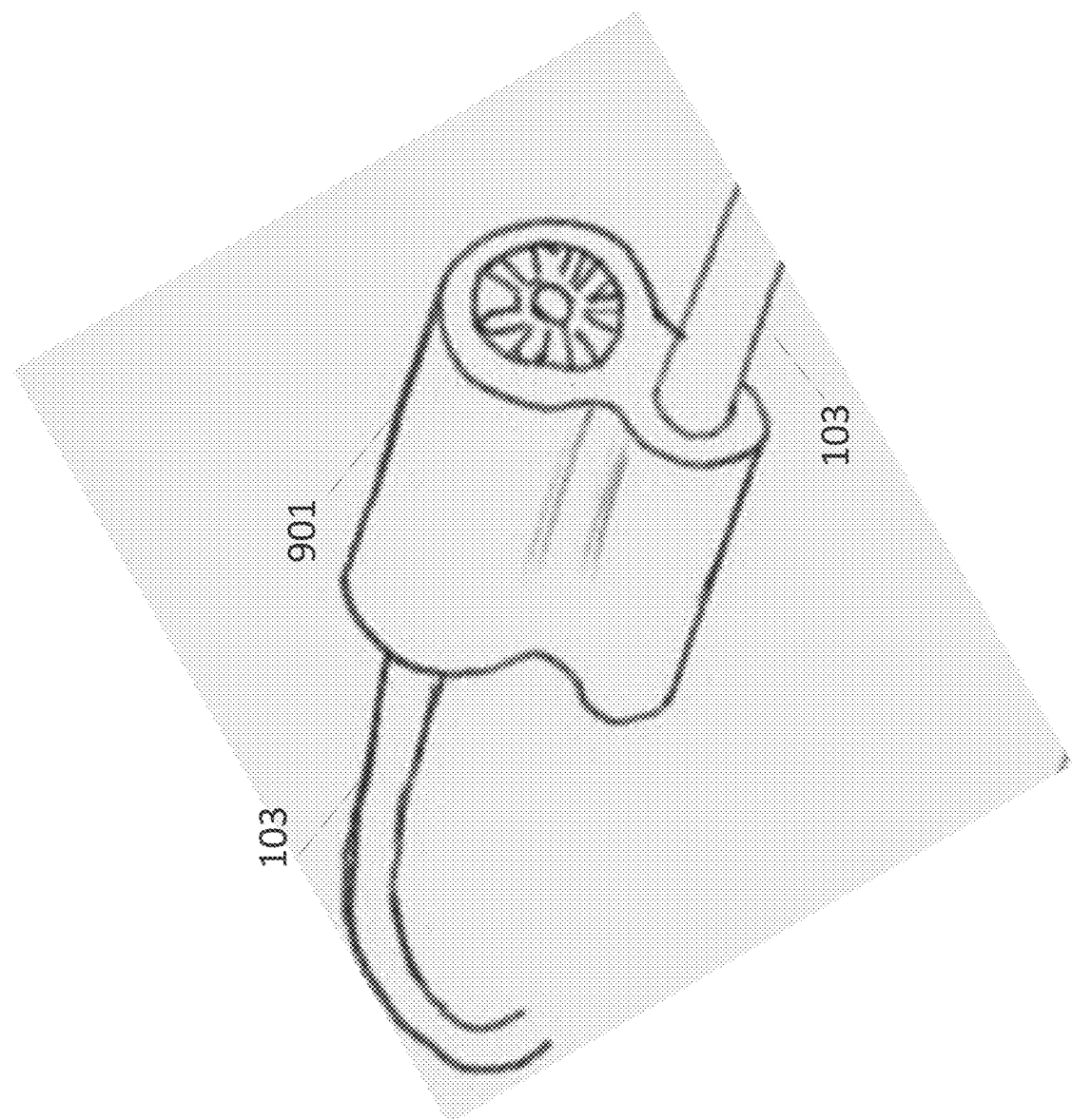
Figure 11D:
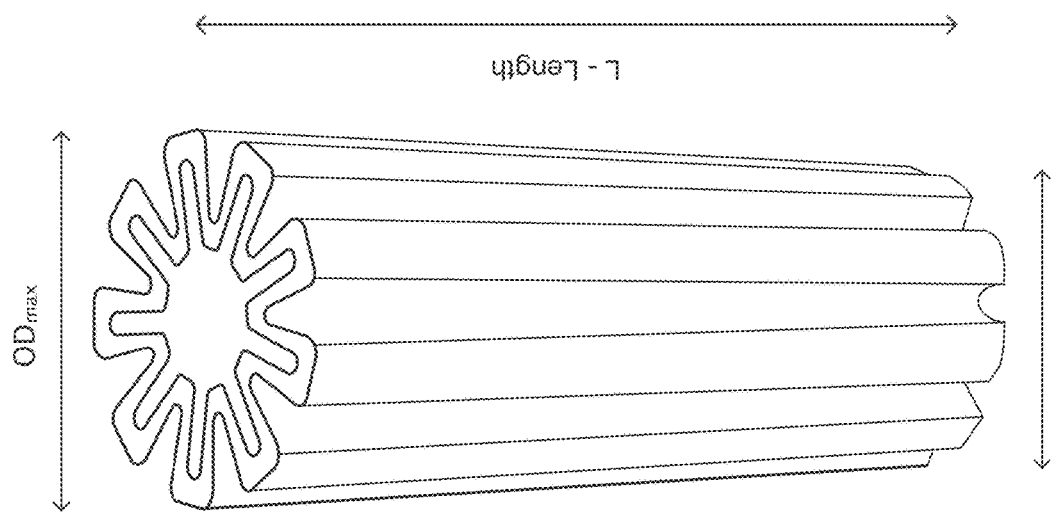
Figure 11C:
Figure 11A:
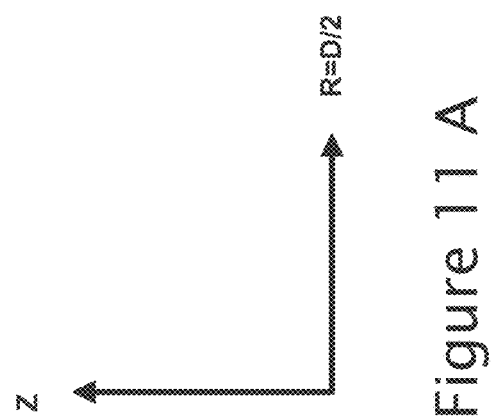
Figure 11B:
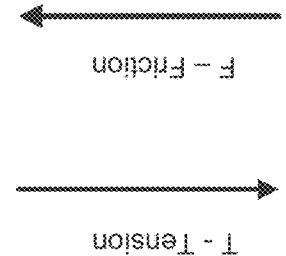

FIG. 9: Cerclage cartridge (901) with surgical cable (103) installed therein.

FIG. 10: Front and side views showing fractured flat bones (102) held in compression by a surgical cable (103). Each end of the cable is secured by a tabbed cartridge (1001) screwed into the flat bone segments.

FIGS. 11 A-D indicates several unique features of the star-shaped collet (202) of FIG. 3A. For reference purposes a coordinate system is shown in FIG. 11 A indicating the positive z axis running from the insertion end of the collet (202) to the exposed end. The direction of the opposing forces on the cable (10) are indicated in FIG. 11 B. Note tensional force T acts in the negative z direction while the frictional force F, (the opposing force), acts in the opposite direction FIG. 11 C is a re-rendering of FIG. 3A with an indication of the outer diameters of the insertion end ($OD_{min}$) and exposed end ($OD_{max}$). Note the outer diameter of the insertion end is smaller than the outer diameter of the exposed end. FIG. 11 D indicates a cross section the collet (202) of FIG. 11 C. Here the inner diameter ($OD_{max}$) of the insertion end is larger than the ($ID_{min}$) of the exposed end.

Figure 12:
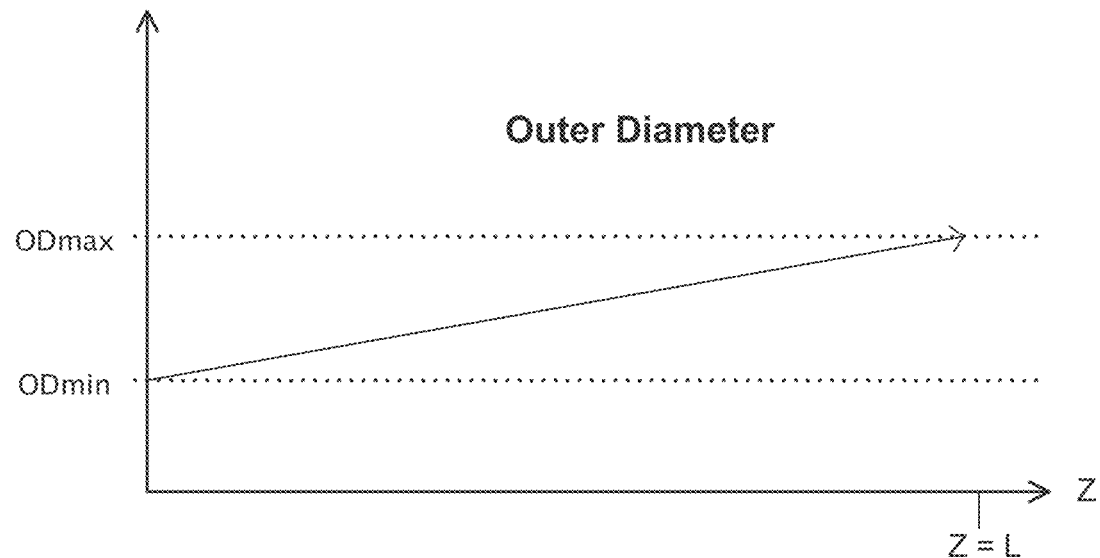
Figure 12:
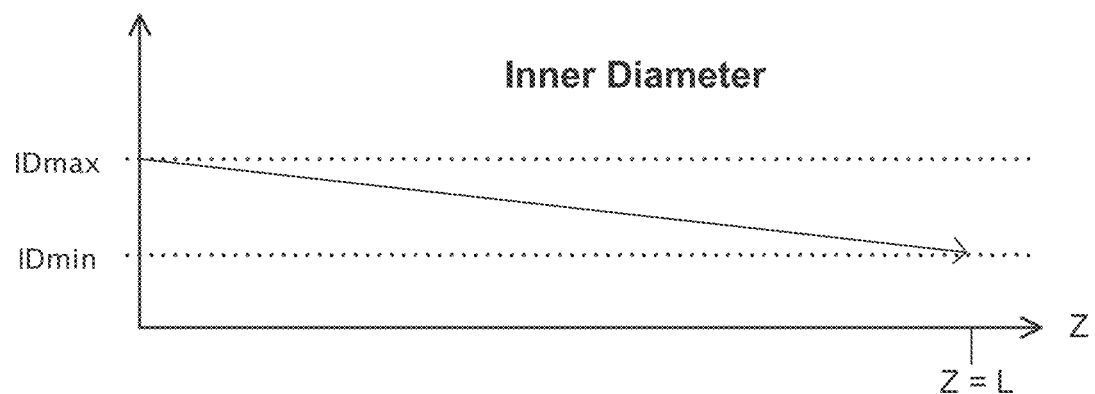

FIGS. 12 A-B are simply a graphical rendition of the above discussion regarding the inner and outer diameters. FIG. 12 A shows the diameter size of the exterior surface of the collet (202) from z=0 (the insertion end) to z=L, (the exposed end). The outer diameter of the insertion end ($OD_{min}$) is minimum at z=0 and the outer diameter of the exposed end ($OD_{max}$) is maximum at z=L. By contrast, FIG. 12 B emphasizes opposing trend of the inner diameter. The inner diameter of the insertion end ($ID_{max}$) is maximum at z==0 and the inner diameter of the exposed end ($ID_{min}$) is minimum at z=L.

Figure 13:
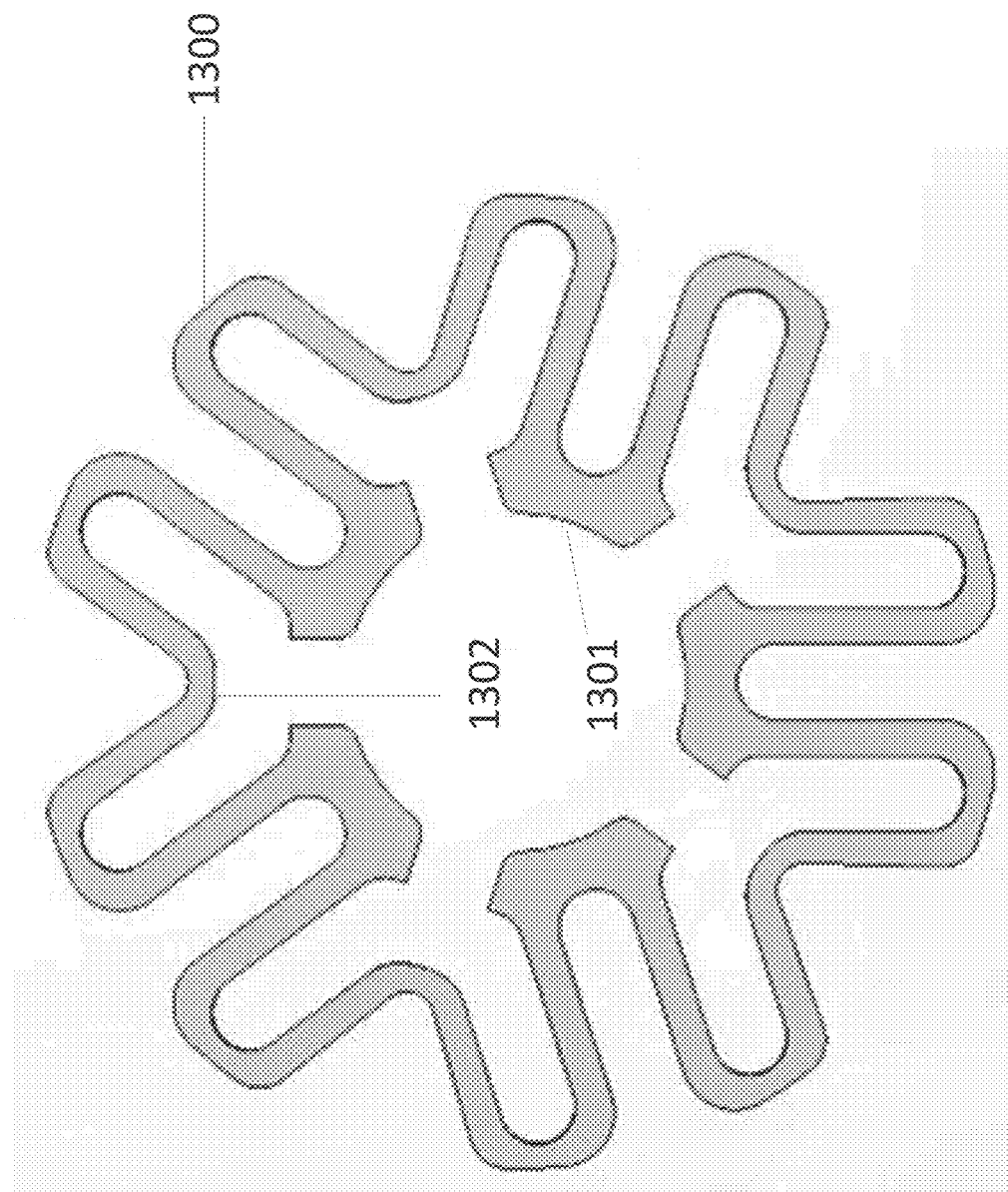

FIG. 13 shows an alternate embodiment of the collet. Here, the outside fingers (1300) are alternately paired with an inside finger (1301) and an intermediate finger (1302). This arrangement enables greater contact with the cable (103) exterior.

FIGS. 1A and 1B illustrate the use of the surgical cartridge. A surgical cable (103) has been threaded though bone fragments (102) as well as the central void (203) of the surgical cartridge (101) A tool (not shown) is then used to draw up, apply the required tension to the surgical cable (103), and seat the surgical cartridge (101) into the outer bone aperture (105). An optional washer (104) may be interspersed between the surgical cartridge (101) and the outer bone aperture (105).

FIG. 2 shows the surgical cartridge (101) in greater detail. The retaining collar (201) holds the star-shaped collet (202) and the central void (203) accommodates the surgical cable (103).

The star-shaped collet (202) is detailed in FIGS. 3A-3E. The perspective view shown in FIG. 3A illustrates the lengthwise features on the exterior of the collet (202). FIGS. 3B-3E illustrate varying stages of deployment of the collet onto the inserted cable (103). FIG. 3B along with the enhanced insert of FIG. 3D, indicate the offset position of the inside surface of the collet wall (303) with respect to the contacting surface (302) of the cable (103) for one collet finger (305). Here, the collet (202) is uncompressed, thus the cable slides freely along the central void (203) of the collet (202). By contrast, FIG. 3C along with the enhanced insert of FIG. 3E, indicate similarly with collet (202) in a compressed (deployed) state. Here, the inside surface of the collet wall (303) is pressed tightly against the contacting surface (302) of the cable (103), thereby preventing movement of the cable (103) along the central void (203) of the collet (202). The ability of the collet (202) to be compressed in this manner while maintaining physical integrity is determined by both the collet (202) material as well as the thickness of the collet wall, the approximate distance between its inner (302) and outer (303) surfaces. Both factors are important design parameters.

A radial cross section of the star-shaped collet (202) with inserted surgical cable (103) is again shown in an uncompressed state in FIGS. 4A-4B, with the corresponding illustrations for the compressed state shown in FIGS. 4C-4D. FIGS. 4A and 4C are simply re-rendered versions of FIGS. 3B and 3C with angular reference axis superimposed thereon. FIGS. 4B and 4D show a notional depiction of applied pressure, P, versus circumferential angle for FIGS. 4A and 4C, respectively. In the uncompressed state, FIGS. 4A-4B, the pressure exerted by the collet (202) on the cable (103) is zero for all angles since there is no contact between the inside surface of the collet wall (303) and the contacting surface (302) of the cable (103). By contrast, the notional depiction of applied pressure, P, versus angle shown in FIG. 4D for the compressed state depicted in FIG. 4C, indicates a regular non-zero behavior. For example, the pressure is minimal at 0°, ±40°, ±80°, ±120°, and ±160° because, at these points the inside surface of the collet wall (303) folds away from the contacting surface (302) of the cable (103). Alternatively, the pressure is maximal at 20°, ±160°, ±100°, ±140°, and 180° since these are points of maximal compression.

Of course, the detailed behavior of a working collet (202) is determined primarily by the shape and number of collet fingers (305). However, an optimal number of fingers is a design parameter that must be determined in balance with the parametrical design consideration of wall thickness. In practice, an optimal balance was achieved using a 5-15 finger design with a wall thickness of 0.005-0.015 inches.

FIGS. 5A-5B show a notional depiction of applied pressure, P, versus angle for various locations (501)-(504) along the length of the collet (202). Although a slight variation in maximal pressure is notionally indicated in the figure, the true variation at any given point is a function of the local values of the tension force and the frictional force.

If such concerns have been adequately addressed, the total force exerted on the cable (103) should be spread over as large an area as possible so that the applied pressure for any given unit surface area is not unduly high, thereby risking tearing and shearing of the delicate fibers covering the cable's outer surface. Consider a length of the cable (10) of FIG. 6. The braided fibers (15) wind around the core (14) in a helical fashion. Some fibers wind to the left while others wind to the right, both groups knit together to make up the braid. The relatively broad fingers of the collet capture this braided arrangement of crossed helical fibers, consistently engaging them in a balanced manner about tihe core circumference as the cable shrinks under tension.

The present invention accomplishes the above goals via a non-intuitive shaping of the inner void of the collet (203) as indicated in FIGS. 11A-11D and 12A-12B. The external conical shape of the collet (202) facilitates physical insertion into the collar (201). However, the surface of the internal central void (203), also conical, angles in the opposing direction. The crimping diameter at the insertion end, where the cable tension is maximum, is larger than the crimping diameter at the exposed end, where the cable tension is minimum. Thus the cable is crimped with less force at the insertion end than at the exposed end.

The reason for this non-intuitive circumstance is due to several factors, all of which are correlated. The central void (203) has an irregular, undulating surface as does the cable. By definition, the frictional force, F acts to opposed any motion due to the tensional force, T. F force is not necessarily constant, i.e., $$F=\mu(z,\varphi)N(z,\varphi)$$

where N is the normal force and $\varphi$ ranges from $-180°$ to $180°$ as shown in FIG. 5B. N, the normal force, can be described simply as the perpendicular component of the "pushing force" of the cable against the interior surface of the collet. Of course, for a surface to be "pushed" against, there must be contact. As indicated in FIG. 5B, the degree of contact between the cable and the collet interior surface is not constant around the interior circumference. Moreover, the surface of the cable is also highly irregular and complex. Thus, any effort to describe the coefficient of friction $\mu$ by an entity as simplistic as a single number, is misleading. At any rate, the result of the optimization procedure disclosed here can be summarized most easily considering the comparative graphs of FIGS. 12 A-B and by stating the limitations in Claim 1, " . . . wherein said truncated cylinder further comprises an insertion end, and an exposed end opposite said insertion end, an outer conical surface and an inner conical surface, said conical surface having a first outer diameter at said insertion end, a second outer diameter at said exposed end, wherein said first outer diameter is smaller than said second outer diameter, said inner conical surface having a first inner diameter at said insertion end, a second inner diameter at said exposed end, wherein said first inner diameter is larger than said second diameter, . . . ".

FIGS. 7-8 illustrate an exemplary installation tool (700) for deployment of the surgical cartridge (101) and with a surgical cable (103) inserted therein. The installation tool (700) is of scissor-like design, having an upper forked member (701) and a lower forked member (702) for gripping the lower ledge of the retaining collar (201) and the upper surface of an inserted collet (202). A auxiliary lever, the cable gripping member (703), provides a positioning conduit through which the surgical cable (103) is threaded and tightened to the required level of tension. The tension is maintained via a tension retaining member (704). The upper forked member (701) and lower forked member (702) not only allow the cartridge assembly to be properly positioned, but also facilitate sliding the collet (202) into the retaining collar (201), thereby providing a gently increasing and uniform grip on a tightened surgical cable (103).

Installation of the surgical cartridge (101) with surgical cable (103) threaded therein occurs as follows.

1. The internally attached surgical cable (103) is threaded through the surgical cartridge (101) assembly,
2. The surgical cartridge (101) is pressed against the bone as the surgical cable (103) is pulled taut,
3. The upper forked member (701) and lower forked member (702) are squeezed together, urging the collet (202) into the throat of retaining collar (201), thereby closing in on the surgical cable (103) inserted therein.
4. The tension on the surgical cable (103) is released,
5. The upper and lower fork members (701), (702) are slid away from the surgical cartridge (101) assembly, and
6. The extraneous cable length is cut.

A cerclage cartridge (901) with an integrated attachment site is shown in FIG. 9. A first end of the surgical cable (103) is crimped into the attachment site by conventional means since, in its untensioned state, the surgical cable (103) is relatively soft and bulky. The free end is then positioned as required and the cable pulled taught. In this tensioned state, the diameter of the surgical cable (103) shrinks and the cable as a whole becomes taut and slippery, requiring the gentle radial compression afforded by the cartridge to effectively secure the remaining end. Consequently, the cerclage cable (901) is particularly well suited to address attachment of the surgical cable (103) in either circumstance.

FIG. 10 shows front and side views of a fractured flat bone (102) held in compression by a surgical cable (103). Tabbed cartridges (1001) screwed into the flat bone segments secure each end of the surgical cable (103).

Alternate embodiments envisioned but not shown include one or more surgical cartridges (101) integrated with other attachment devices such as a bone plate. Indeed, reconstruction techniques may include one or several surgical cartridges securing a network of surgical cables (103) and other attachment devices. In addition, the surgical cartridge (103) can be used to secure other medical tethers, such as (for instance), spider silk.

Recalling the objectives stated in the introductory section of this disclosure, the present invention provides a biomedically compatible gripping device capable of radial collapse in accordance with the shrinkage of nylon or other polymeric material cored surgical cable undergoing tension while maintaining a firm grip throughout the process. Moreover, it provides a gripping device capable of maintaining a grip on the outer surface of a slippery delicate cable, the grip being approximately uniform along both the length and circumference of the cable. It also provides a gripping device capable of maintaining a grip, yet not damage, a delicate cable under high tension for a period of time adequate for as the healing process to occur.

While several illustrative embodiments of the invention have been shown and described, numerous variations and alternate embodiments will occur to those skilled in the art, and can be made without departing from the spirit and scope of the invention as defined in the appended claims.

The invention claimed is:

1. A suture anchor comprising:
   a body having a longitudinal axis, a first end, and a second end spaced from said first end along said longitudinal axis, said body comprising:
   a cylindrical wall having an outer surface and an inner surface, said inner surface defining a central void to receive a single suture there through, the single suture having a central axis and an outer suture circumference with nine regions evenly distributed about the central axis of the single suture, said central void having a cross-section with a size, said cylindrical wall being configured to be radial expandable and radially collapsible,
   wherein said inner surface is operable to move radially outward to increase said size of said cross-section to receive the single suture therein and to move radially inward to decrease said size of said cross-section,
   wherein, when a portion of the single suture is in said central void and said cylindrical wall is radially collapsed onto the portion of the single suture, said inner surface is configured to contact each of the nine regions of the single suture and to impart radially inward compression on the portion of the single suture about the outer suture circumference to thereby retain the single suture therein,
   wherein said inner surface includes multiple grooves, each groove of said multiple grooves is spaced about a longitudinal axis of said central void and extends between said first end and said second end of said body,
   wherein said multiple grooves form a set of inside fingers, and said outer surface includes a set of outside fingers, and
   wherein each of said set of outside fingers includes a hinge with a hinge axis parallel to the central axis of the single suture.

2. The suture anchor of claim 1 wherein said multiple grooves comprise a first groove, a second grove, a third groove, and a fourth groove.

3. The suture anchor of claim 2, wherein said inner surface comprises:
   a first portion positioned between said first groove and said second grove; and
   a second portion of said inner surface positioned between said third and fourth grooves.

4. The suture anchor of claim 1, wherein said body is configured to receive the single suture through said central void of said body such that said body provides greater than or equal to 2500 psi over an area of the suture measuring 0.05 square inches or less.

5. The suture anchor of claim 1, wherein said set of outside fingers comprises at least 7 radial fingers.

6. The suture anchor of claim 1, further comprising a retaining collar configured to receive said body.

7. The suture anchor of claim 6, wherein said first end forms an insertion end into said retaining collar, and wherein a minimum transverse dimension of said central void at said first end is greater than or equal to a minimum transverse dimension of said central void at said second end.

8. The suture anchor of claim 7, wherein a maximum transverse dimension of said outer surface at said first end is less than or equal to a maximum transverse dimension of said outer surface at said second end.

9. The suture anchor of claim 6, wherein said retaining collar is configured to compress said first end of said body such that a radial arrangement of compressive fingers is configured to impart radial compression on the single suture inserted within said central void of said body when said body is positioned in said retaining collar.

10. The suture anchor of claim 6, wherein each groove of said multiple grooves extends radially outward from said longitudinal axis of said central void of said body.

11. The suture anchor of claim 6, wherein said retaining collar comprises:
   a channel;
   a first end configured to be inserted into a bone; and
   a second end having a flange extending outward from said channel of said retaining collar, said flange configured to contact a surface of the bone such that said flange limits movement of said retaining collar in a first direction toward the bone.

12. The suture anchor of claim 11, wherein said channel of said retaining collar has a maximum transverse dimension at said first end of said retaining collar that less than said maximum transverse dimension of said outer surface of said body at said first end of said body.

13. The suture anchor of claim 11, wherein said first end of said retaining collar is configured to compress said first end of said body such that each groove of said multiple grooves applies a radially inward pressure onto the single suture extending through said central void of said body.

14. The suture anchor of claim 1, in combination with a tool for deployment of said suture anchor, said tool comprising:
   an upper forked member and a lower forked member, said upper forked member and said lower forked member configured in a scissor-like fashion, said lower forked member is configured to secure and position said suture anchor;
   an auxiliary lever operable to grip a suture associated with said suture anchor, said auxiliary lever comprises a positioning conduit operable to adjust a tension level of the single suture; and
   a tension retaining member configured to maintain a first level of tension on the single suture.

15. The suture anchor of claim 14, wherein said outside fingers of said outer surface includes a radial arrangement.

16. The suture anchor of claim 15, wherein said outside fingers comprise at least 7 outside fingers.

17. A suture anchor comprising:
   a body having a longitudinal axis, a first end, and a second end spaced from said first end along said longitudinal axis, the body including:
   a cylindrical wall having an outer surface and an inner surface, said inner surface defining a central void to receive a suture there through, the suture having an outer suture circumference and a central suture axis, said central void having a cross-section with a size, said cylindrical wall including a hinge configured to facilitate radial expansion and radial collapse of said cylindrical wall, said hinge including a hinge axis that is substantially parallel to the central suture axis of the suture,
   wherein said inner surface is operable to move radially outward to increase said size of said cross-section to receive the suture therein and to move radially inward to decrease said size of said cross-section,
   wherein, when a portion of the suture is in said central void and said cylindrical wall is radially collapsed onto the portion of the suture, said inner surface is configured to contact and impart radially inward compression on the portion of the suture to thereby retain the suture therein,
   wherein said inner surface includes multiple grooves, each groove of said multiple grooves is spaced about a longitudinal axis of said central void and extends between said first end and said second end of said body, and
   wherein a first one of a set of outside fingers includes said hinge, and wherein outside fingers of said set other than said first one each includes a hinge with a hinge axis parallel to the central suture axis.

18. The suture anchor of claim 17 wherein said inner surface is configured to contact and to impart radially inward compression on the portion of the suture about a majority of the outer suture circumference to thereby retain the suture therein.

19. The suture anchor of claim 17 wherein said hinge is a living hinge with said hinge axis being a living hinge axis.

20. The suture anchor according to claim 17 wherein said multiple grooves form a set of inside fingers, and said outer surface includes said set of outside fingers.

21. The suture anchor of claim 17 comprising a retaining collar configured to receive said body.

22. The suture anchor of claim 21, wherein said retaining collar is configured to compress said first end of said body such that a radial arrangement of compressive fingers is configured to impart radial compression on the suture inserted within said central void of said body when said body is positioned in said retaining collar.

23. The suture anchor of claim 21, wherein said retaining collar includes:
   a channel;
   a first end configured to be inserted into a bone; and
   a second end having a flange extending outward from said channel of said retaining collar, said flange configured to contact a surface of the bone such that said flange limits movement of said retaining collar in a first direction toward the bone.

* * * * *

UNITED STATES PATENT AND TRADEMARK OFFICE
CERTIFICATE OF CORRECTION

| | |
|---|---|
| PATENT NO. | : 11,839,366 B2 |
| APPLICATION NO. | : 16/429456 |
| DATED | : December 12, 2023 |
| INVENTOR(S) | : Terry Mattchen |

It is certified that error appears in the above-identified patent and that said Letters Patent is hereby corrected as shown below:

In the Claims

Claim 12, Column 11, Line 19:
"at said first end of said retaining collar that less than said"
Should be:
--at said first end of said retaining collar that is less than said--

Signed and Sealed this
Thirteenth Day of February, 2024

Katherine Kelly Vidal
*Director of the United States Patent and Trademark Office*